United States Patent
Blade et al.

(12)
(10) Patent No.: US 6,423,731 B2
(45) Date of Patent: Jul. 23, 2002

(54) INDOLE DERIVATIVES AS PRODRUGS OF 5-HT$_1$-LIKE RECEPTOR AGONISTS

(75) Inventors: Robert John Blade; Yih Sang Pang, both of Stevenage; David Lawrence Selwood, London, all of (GB)

(73) Assignee: Zeneca Limited (GB)

( * ) Notice: Subject to any disclaimer, the term of this patent is extended or adjusted under 35 U.S.C. 154(b) by 0 days.

(21) Appl. No.: 09/759,586

(22) Filed: Jan. 12, 2001

Related U.S. Application Data

(63) Continuation of application No. 09/360,387, filed on Jul. 23, 1999, now abandoned, which is a continuation of application No. 08/737,759, filed as application No. PCT/GB95/01249 on May 31, 1995, now Pat. No. 5,962,486.

(30) Foreign Application Priority Data

Jan. 6, 1994 (EP) .............................. 94303928

(51) Int. Cl.$^7$ .............................. A61K 31/42
(52) U.S. Cl. ...................................... 514/376
(58) Field of Search .......................... 514/376

(56) References Cited

U.S. PATENT DOCUMENTS

| | | | | |
|---|---|---|---|---|
| 5,348,968 A | * | 9/1994 | Lavielle et al. | |
| 5,399,574 A | * | 3/1995 | Robertson et al. | |
| 5,409,941 A | | 4/1995 | Nowatkowski et al. | 514/339 |
| 5,466,699 A | * | 11/1995 | Robertson et al. | |

FOREIGN PATENT DOCUMENTS

| | | | |
|---|---|---|---|
| EP | 313397 | 4/1989 | ......... C07D/403/06 |
| EP | 610134 | 8/1994 | ......... C07D/403/06 |
| WO | WO 91/18897 | 12/1991 | ......... C07D/413/06 |
| WO | WO 92/13856 | 8/1992 | ......... C07D/417/14 |
| WO | WO93/21182 | 10/1993 | ......... C07D/417/12 |

OTHER PUBLICATIONS

Teranishi et al., "Facile synthesis, etc.," CA 122:81057 (1994).

Garcia et al., "The regiospecific Pummerer–like, etc.," CA 108:221547 (1988).

Fishwick et al., "Regio– and chemoselect alkylation etc.," CA 115:92002 (1991).

\* cited by examiner

*Primary Examiner*—Jerome O. Goldberg
(74) *Attorney, Agent, or Firm*—Kenneth F. Mitchell

(57) ABSTRACT

A method for the prophylaxis or treatment of conditions for which 5-HT$_1$-like agonists are indicated comprising the administration of therapeutically-effective amount of compounds of formula (I)

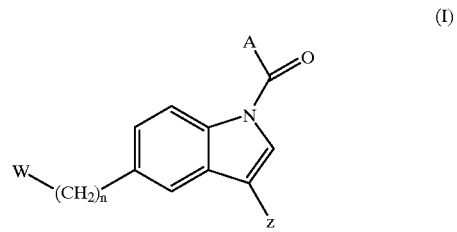

wherein A, W, Z and n are as defined in the specification.

5 Claims, No Drawings

INDOLE DERIVATIVES AS PRODRUGS OF 5-HT$_1$-LIKE RECEPTOR AGONISTS

This is a continuation of application Ser. No. 09/360,387 filed Jul. 23, 1999, which is a Continuation of application No. 08/737,759 filed Nov. 22, 1996, now U.S. Pat. No. 5,962,486 which is a National Phase of International Application No. PCT/GB95/01249 filed May 31, 1995.

The present invention is concerned with new chemical compounds, their preparation, pharmaceutical formulations containing them and their use in medicine, particularly the prophylaxis and treatment of migraine.

Receptors which mediate the actions of 5-hydroxytryptamine (5- have been identified in mammals in both the periphery and the brain. Currently, as many as seven 5-HT receptor classes are proposed (Humphrey et al., Trends Pharmac Sci., 14, 233-236, 1993), although only the classes nominated 5-HT$_1$, 5-HT$_2$, 5-HT$_3$, and 5-HT$_4$ have established physiological roles. European Patent Specification 0313397 describes a class of 5-HT agonists which act selectively at a particular subtype of 5-HT$_1$ receptor and are effective therapeutic agents for the treatment of clinical conditions in which a selective agonist for this type of receptor is indicated. For example, the receptor in question mediates selective cranial arterial vasoconstriction and inhibition of plasma protein extravasation into the dura mater evoked by activation of the Vth (trigeminal) nerve. The compounds described in the European specification are therefore beneficial in the treatment or prophylaxis of conditions wherein these actions are indicated, for example, migraine, a condition associated with and/or neurogenically-evoked inflammation dilation of the cranial vasculature. However, it is within the scope of the earlier application that the target tissue may be arty tissue wherein action is mediated by 5-HT$_1$ receptors of the type referred to above.

EP-A-0486666 discloses a class of compounds having exceptional activity at the 5-HT$_1$ receptor mentioned above and excellent absorption following oral dosing. These properties render the compounds particularly useful for certain medical applications, notably the prophylaxis and treatment of migraine, cluster headache and headache associated with vascular disorders, hereinafter referred to collectively as "migraine".

There has now been discovered a class of compounds which, although having relatively little activity themselves at the 5-HT$_1$ receptor, act as prodrugs releasing active compound after administration. Such compounds thereby provide active compound with improved metabolic stability and bioavailability.

Thus, according to a fist aspect of the present invention there is provided a compound of formula (I):

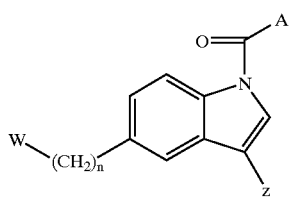

(I)

wherein

A is C$_{1-6}$ alkyl, —O—C$_{1-6}$ alkyl, or —O-phenyl, or phenyl, optionally substituted by C$_{1-3}$ alkyl or halogen;

n is an integer of from 0 to 3;

W is a group of formula (i), (ii) or (iii)

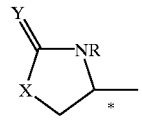

(i)

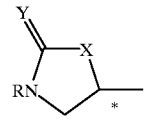

(ii)

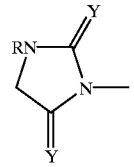

(iii)

wherein R is hydrogen or C$_{1-4}$ alkyl, X is —O—, —S—, —NH—, or —CH$_2$—, Y is oxygen or sulphur and the chiral centre * in formula (i) or (ii) is in its (S) or (R) form or is a mixture thereof in any proportions; and Z is a group of formula (iv), (v) or (vi)

(iv)

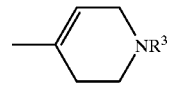

(v)

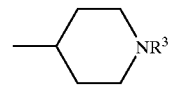

(vi)

wherein R$^1$ and R$^2$ are independently selected from hydrogen and C$_{1-4}$ alkyl and R$^3$ is hydrogen or C$_{1-4}$ alkyl;

and salts, solvates and physiologically functional derivatives thereof.

Preferably W is a group of formula (i) and Z is a group of formula (iv)

In another aspect the present invention provides a compound of the formula (Ia)

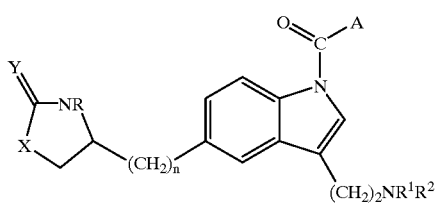

(Ia)

wherein

A is C$_{1-6}$ alkyl, —O—C$_{1-6}$ alkyl, —O-phenyl or phenyl, optionally substituted by C$_{1-3}$ alkyl or halogen;

n is an integer from 0 to 3;

R is hydrogen or C$_{1-4}$ alkyl;

X is —O—, —S—, —NH—or —CH$_2$—;

Y is oxygen or sulphur, and

R$^1$ and R$^2$ are independently selected from hydrogen and C$_{1-4}$ alkyl and salts, solvates and physiologically functional derivatives thereof.

Preferred compounds of formula (Ia) are those wherein n is 1, X is —O— and Y is oxygen. Compounds wherein R$^1$ and R$^2$ are independently selected from hydrogen and methyl are preferred, with compounds wherein R$^1$ and R$^2$ are both methyl being particularly preferred.

Compounds of formula (I) and (Ia) are capable of existing as optical isomers. All such isomers, individually and as mixtures, are included within the scope of the present invention.

Examples of preferred compounds of the invention include:

(1) 4-[1-Benzoyl-3-[2-(dimethylamino)ethyl]indol-5-ylmethyl]oxazolidin-2-one acetate;

(2) 4-[1-Pivaloyl-3-[2-(dimethylamino)ethyl]indol-5-ylmethyl]oxazolidin-2-one acetate;

(3) 4-[1-(2'-toluoyl)-3-[2-(dimethylamino)ethyl]indol-5-ylmethyl]oxazolidin-2-one acetate;

(4) 4-[1-Benzyloxycarbonyl-3-[2-(dimethylamino)ethyl] indol-5-ylmethyl]oxazolidin -2-one;

(5) 4-[1-t-Butyloxycarbonyl-3-[2-(dimethylamino)ethyl] indol-5-ylmethyl]oxazolidin-2-one acetate; and (6) 4-[1-Acetyl-3-[2-(dimethylamino)ethyl]indol-5-ylmethyl]oxazolidin-2-one acetate.

Physiologically acceptable salts are particularly suitable for medical applications because of their greater aqueous solubility relative to the parent, ie basic, compounds. Such salts must clearly have a physiologically acceptable anion. Suitable physiologically acceptable salts of the compounds of the present invention include those derived from acetic, hydrochloric, hydrobromic, phosphoric, malic, maleic, fumaric, citric, sulphuric, lactic, or tartaric acid The succinate and chloride salts are particularly preferred for medical purposes. Salts having a non-physiologically acceptable anion arc within the scope of the invention as useful intermediates for the preparation of physiologically acceptable salts and/or for use in non-therapeutic, for example, in vitro, situations.

According to a third aspect of the present invention, there is provided a compound of formula (I) or (Ia) or a physiologically acceptable salt, solvate, or physiologically functional derivative thereof for use as a therapeutic agent, specifically as a "5-HT$_1$-like" receptor agonist, for example, as a carotid vasoconstrictor or as an inhibitor of neurogenic inflammation in the prophylaxis and treatment of migraine. As indicated, however, target organs for the present compounds other than the carotid vasculature are within the scope of the present invention.

The amount of a compound of formula (I) or (Ia), a salt or solvate thereof, which is required to achieve the desired biological effect will depend on a number of factors such as the specific compound, the use for which it is intended, the means of administration and the recipient. A typical daily dose for the treatment of migraine may be expected to lie in the range 0.01 to 5 mg per kilogram body weight. Unit doses may contain from 1 to 100 mg of a compound of formula (I), for example, ampoules for injection may contain from 1 to 10 mg and orally administrable unit dose formulations such as tablets or capsules may contain from 1 to 100 mg. Such unit doses may be administered one or more times a day separately or in multiples thereof. An intravenous dose may be expected to lie in the range 0.01 to 0.15 mg/kg and would typically be administered as an infusion of from (0.0003 to 0.15 mg per kilogram per minute. Infusion solutions suitable for this purpose may contain from 0.01 to 10 mg/ml.

When the active compound is a salt or solvate of a compound of formula (I) the dose is based on the cation (for salts) or the unsolvated compound.

Hereinafter references to "compound(s) of formula (I) or (Ia)" will be understood to include physiologically acceptable salts and solvates thereof According to a fourth aspect of the present invention, therefore, there are provided pharmaceutical compositions comprising, as active ingredient, at least one compound of formula (I) or (Ia) and/or a pharmacologically acceptable salt or solvate thereof together with at least one pharmaceutical carrier or excipient. These pharmaceutical compositions may be used in the prophylaxis or treatment of clinical conditions for which a "5-HT$_1$-like" receptor agonist is indicated, for example, migraine. The carrier must be pharmaceutically acceptable to the recipient and must be compatible with, i.e. not have a deleterious effect upon, the other ingredients in the composition. The carrier may be a solid or liquid end is preferably formulated with at least one compound of formula (I) or (Ia) as a unit dose formulation, for example, a tablet which may contain from 0.05 to 95% by weight of the active ingredient. If desired, other physiologically active ingredients may also be incorporated in the pharmaceutical compositions of the invention.

Possible formulations include those suitable for oral, sublingual, buccal, parenteral (for example, subcutaneous, intramuscular, or intravenous), rectal, topical and intranasal administration. The most suitable means of administration for a particular patient will depend on the nature and severity of the condition being treated and on the nature of the active compound, but, where possible, oral administration is preferred.

Formulations suitable for oral administration may be provided as discrete units, such as tablets, capsules, cachets, or lozenges, each conning a predetermined amount of the active compound: as powders or granules; as solutions or suspensions in aqueous or non-aqueous liquids; or as oil-in-water or water-in-oil emulsions.

Formulations suitable for sublingual or buccal administration include lozenges comprising the active compound and, typically, a flavoured base, such as sum and acacia or tragacanth, and pastilles comprising the active compound in an inert base, such as gelatin and glycerin or sucrose and acacia.

Formulations suitable for parenteral administration typically comprise sterile aqueous solutions containing a predetermined concentration of the active compound; the solution is preferably isotonic with the blood of the intended recipient. Although such solutions are preferably administered intravenously, they may also be administered by subcutaneous or intramuscular injection.

Formulations suitable for rectal administration are preferably provided as unit-dose suppositories comprising the active ingredient and one or more solid carries forming the suppository base, for example, cocoa butter.

Formulations suitable for topical or intranasal application include ointments, creams, lotions, pastes, gel, sprays, aerosols and oils. Suitable carriers for such formulations include petroleum jelly, lanolin, polyethylene glycols, alcohols, and combinations thereof The active ingredient is typically present in such formulations at a concentration of from 0.1 to 15% w/w.

The formulations of the invention may be prepared by any suitable method, typically by uniformly and intimately admixing the active compound(s) with liquids or finely divided solid carriers, or both in the required proportions and then if necessary, shaping the resulting mixture into the desired shape.

For example, a tablet may be prepared by compressing an intimate mix comprising a powder or granules of the active ingredient and one or more optional ingredients, such as a binder, lubricant, inert diluent, or surface active dispersing agent, or by moulding an intimate mixture of powdered active ingredient and inert liquid diluent.

Aqueous solutions for parenteral administration are typically prepared by dissolving the active compound in sufficient water to give the desired concentration and then rendering the resulting solution sterile and isotonic.

Thus, according to a fifth aspect of the present invention, there is provided the use of a compound of formula (I) or (Ia) in the preparation of a medicament for the prophylaxis or treatment of a clinical condition for which a "5-HT$_1$-like" receptor agonist is indicated for example; migraine.

According to a sixth aspect, there is provided a method for the prophylaxis or treatment of a clinical condition in a mammal, for example, a human, for which a "5-HT$_1$-like" receptor agonist is indicated, for example, migraine, which comprises the administration to said mammal of a therapeutically effective amount of a compound of formula (I) or (Ia) or of a physiologically acceptable salt, solvate, or physiologically functional dative thereof.

The present invention also provides, in a seventh aspect, a process for the preparation of a compound of formula (I) or (Ia) This process comprises reaction of a compound of formula (II).

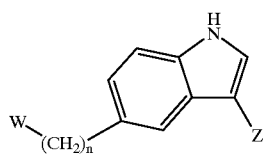

(II)

wherein W, Z and n are as hereinbefore defined, with a compound of formula (III)

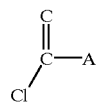

(III)

wherein A is as hereinbefore defined.

The reaction is preferably carried out in the presence of a base such as an organic base, for example triethylamine, pyridine or Hunig's base, or an inorganic base for example sodium hydride or potassium carbonate. Sodium hydride is preferred. The reaction may be cared out in polar aprotic solvents such as dimethylformamide, dimethylsulphoxide or in chlorinated solvents such as dichloromethane. Dimethylformamide is the preferred solvent The reaction may be carried out in the temperature range 0- 100°. 0° to room temperature is preferred.

Where it is desired to prepare a compound of formula (Ia), a compound of formula (IIa)

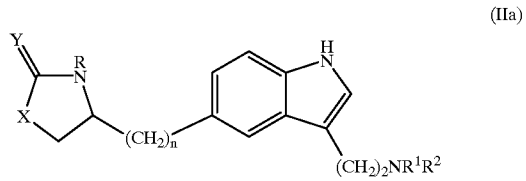

(IIa)

wherein X, Y, R, n, $R^1$ and $R^2$ are as hereinbefore defined may be used in place of the compound of formula (II).

Compounds of formula (II) and (IIa) can be made according to the methods described in EP A-0486666, incorporated herein by reference. Compounds of formula (III) are commercially available or can be readily prepared by those skilled in the art using known methods.

Alternatively, compounds of formula (I) or (Ia) may be prepared by reaction of a compound of formula (II) or (IIa) with a compound of formula (IV)

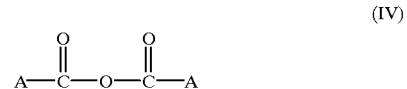

(IV)

wherein A is as hereinbefore defined.

The reaction is preferably carried out in the presence of a base such as an organic base, for example triethylamine, pyridine or dimethylamino pyridine or an inorganic base for example sodium hydride or potassium carbonate. Dimethylaminopyridine is preferred when it is desired to make the compound 4-[1-t-Butyloxycarbonyl-3-[2-(dimethylamino) ethyl]indol-5-ylmethyl] oxazolidin-2-one acetate. Sodium hydride is the preferred base when it is desired to make the compound 4-[1-Acetyl-3-[2-(dimethylamino)ethyl]indol-5-ylmethyl]oxazolidin-2-one acetate. The reaction may be carried out in polar aprotic solvents such as acetonitrile, dimethylformamide, dimethylsulphoxide or in chlorinated solvents such as dichloromethane. Acetonitrile is the preferred solvent for synthesis of the compound 4-[1-t-Butyloxycarbonyl-3-[2-(dimethylamino)ethyl]indol-5-yl methyl]oxazolidin-2-one acetate. Dimethylformamide is the preferred solvent for synthesis of the compound 4-[1-Acetyl-3-[2-(dimethylamino)ethyl]indol-5-ylmethyl] oxazolidin-2-one acetate. The reaction may be carried out in the temperature range 0-100°. 0° to room temperature is preferred.

Compounds of formula (IV) are commercially available or can be readily prepared by those skilled in the art using known methods.

Salts, solvates and physiologically functional derivatives of Compounds of formula (I) or (Ia) may be prepared from compounds of formula (I) or (Ia) using standard techniques known in the art.

The invention will now be described, by way of illustration only, by the following examples:

EXAMPLE 1

4-[1-Benzoyl-3-[2-(dimethylamino)ethyl]indol-5-ylmethyl] oxazolidin-2-one acetate 4-{1-H-3-[2(Dimethylamino)ethyl]indol-5-ylmethyl} oxazolidin-2-one (1 g, 3.49 mmol) in anhydrous dimethylformamide (DMF) was added by syringe to a suspension of hexane washed sodium hydride (132 mg of 60% dispersion, 3.30 mmol) in anhydrous DMF (5 ml) at room temperature. The gel-like slurry was stirred at room temperature for 1 hour, benzoyl chloride (405 μl, 3.49 mmol) was added and the reaction stirred for a further hour. Sodium hydride (132 mg of 60% dispersion) added and the whole stirred overnight at room temperature. The reaction mire was partitioned between ethyl acetate and saturated aqueous ammonium chloride. The organic phase was washed with brine and dried over magnesium sulphate. The crude product was purified by (a) chromatography on silca, eluting with dichloromethane/methanol/ammonia (90:10:0.5) and then (b) Reverse phase HPLC on a $C^8$ column eluting with acetonitrile/water/ammonium acetate to give, after freeze/drying, the title product as a colourless amorphous solid (with 1.0 ACOH). $^1$H NMR (200 MH$_z$, d$_6$ DMSO); 8.26 (1H, d, J=9H$_z$); 7.54-7.80 (7H, m,); 7.26 (1H, d, J=9Hz); 7.22 (1H, s); 4.28 (1H, t, J=7.5Hz); 4.08 (2H, m); 2.92 (2H, m); 2.79 (2H, t); 2.53 (2H, t); 2.18 (6H, s).

The following compounds of examples 2-4 were prepared using a method analogous to that described in example 1:

EXAMPLE 2
4-[1-Pivaloyl-3-[2-(dimethylamino)ethyl]indol-5-ylmethyl]oxazolidin-2-one acetate Amorphous colourless solid (with 1.35 mol ACOH)

$^1$H NMR (200 MH$_Z$, d$_6$ DMSO); 8.28 (1H,d,J=9Hz); 7.89 (1H, s); 7.78 (1H, s); 7.47 (1H, s); 7.18 (1H, d, J=9Hz); 4.28 (1H, t, J=7.5Hz); 4.07 (2H, m); 2.89 (2H, m) 2.86 (2H, t); 2.58 (2H, t); 2.25 (6H, s); 1.46 (9H, s).

EXAMPLE 3
4-[1-(2-toluoyl)-3-[2-(dimethylamino)ethyl]indol-5-ylmethyl]oxazolidin-2-one acetate Amorphous colourless solid mp 51.5-54° (with 0.7 ACOH)

$^1$H NMR(200 MH$_Z$,d$_6$ DMSO); 8.05 (1H, d, J=9Hz); 7.35-7.59 (5H, m); 7.25 (1H, d, J =9Hz); 6.94 (1H, s); 4.28 (1H, t, J=7.5Hz); 4.09 (2H, m); 2.92 (2H, m); 2.77 (2H, t); 2.56 (2H, t); 2.24 (6H, s); 2.18 (3H, s).

Calc. for $C_{24}H_{27}N_3O_3$, 0.25 $H_2O$. 0.68 ACOH; C:65.73, H N:8.83.

Found C. 65.68, H:6.89, N:9.08.

Accurate mass; 405.20305 ($C_{24}H_{27}N_3O_3$)

EXAMPLE 4
4-[1-Benzyloxycarbonyl-3-[2-(dimethylamino)ethyl]indol-5-yl methyl]oxazolidin-2-one Amorphous colourless solid $^1$H NMR (200 MH$_z$, d$_6$ DMSO); 7.97 (1H, d, 9Hz); 7.78 (1H, s); 7.38-7.57 (7H, m); 7.21 (1H, d, J=9Hz); 5.46 (2H, s); 4.27 (1H, t, J=7.5Hz); 4.07 (2H, m); 2.88 (2H, m); 2.70 (2H, t); 2.56 (2H, t); 2.22 (6H, s).

EXAMPLE 5
4-[1-t-Butyloxycarbonyl-3 -[2-(dimethylamino)ethyl]indol-5-ylmethyl]oxazolidin-2-one acetate 4-{1-H-3-[2(Dimethylamino)ethyl]indol-5-ylmethyl}oxazolidin-2-one (1.5 g, 5.23 mmol) and 4-dimethylaminopyridine (61 mg) dissolved in anhydrous acetonitrile (20 ml) and dry DMF (5 ml). Di-t-butyl dicarbonate (1.25 g, 5.75 mmol) in dry acetonitrile (10 ml) was added, with stirring over 1.5 hours. The reaction mixture was concentrated in vacuo and partitioned between water and ethyl acetate. Organic phase washed with water and dried and residue purified by (a) chromatography on silica, eluting with dichloromethane/methanol/ammonia (90.10:1) and then (b) Reverse phase HPLC on a $C^8$ column eluting with acetonitrile/water/ammonium acetate to give after feeze-drying the title compound as colourless amorphous solid (with 0.6 ACOH)

$^1$H NMR (200 MH$_z$, d$_6$, DMSO); 7.96 (1H, d, J=9.5Hz); 7.77 (1H, s); 7.48 (1H, s), 7.46 (1H, d); 7.20 (1H, d, J=9.5Hz); 4.27 (1H, t); 4.06 (2H, m); 2.88 (2H, m); 2.78 (2H, t); 2.55(2H, t) 2.23 (3H, s); 1.53 (9H, s).

Accurate mass; 387.2136 ($C_{21}H_{29}N_3O_4$)

EXAMPLE 6
4-[1-Acetyl-3-[2-(dimethylamino)ethyl]indol-5-ylmethyl]oxazolidin-2-one acetate 4-{1-H-3-[-2-(Dimethylamino)ethyl]indol-5-ylmethyl}oxazolidin-2-one (1 g, 3.48 mmol) in anhydrous dimethylformamide (DMF) was added by syringe to a suspension of sodium hydride (139 mg of 60% dispersion, 3.48 mmol) in anhydrous DMF (20 ml) at room temperature under nitrogen. The reaction mixture was stirred at room temperature for 2 hours and then cooled to 5° C. Acetic anhydride (0.355 g, 3.48 mmol) in anhydrous tetahydrofuran (2 ml) was added to the reaction mixture dropwise over 10 minutes keeping the temperature at 5° C. stirring continued at this temperature for one hour. The reaction mixture was partitioned between chloroform and saturated aqueous ammonium chloride The organic phase was dried over magnesium sulphate and the crude product purified by Reverse Phase HPLC on a C8 column eluting with acetonitrile/water/ammonium acetate Freeze drying afforded the title compound.

$^1$H NMR (200 MHz, d$_6$ DMSO); 8.20 (1H, d); 7.77 (1H, s); 7.62 (1H, s); 7.46 (1H, d), 7.18 (1H, d); 4.28 (1H, t); 4.08 (2H, m); 2.90 (2H, m); 2.79 (2H, t); 2.57 (3H, s); 2.53 (2H, t); 2.25 (6H, s); 1.88 (3H, s)

Calc. for $C_{18}H_{23}N_3O_3$. $CH_3COOH$, 1.09 $H_2O$; C; 58.73; H, 7.14; N, 10.27 Found C, 58.62; H, 7.28; N, 10.38.

PHARMACEUTICAL FORMULATION EXAMPLES

In the following Examples, the "active ingredient" may be any compound of formula (I) or (Ia) and/or a physiologically acceptable salt, solvate, or physiologically functional derivative thereof.

| (1) Tablet formulations | | | |
|---|---|---|---|
| | Mg/tablet | | |
| (i) Oral | A | B | C |
| Active ingredient | 25 | 25 | 25 |
| Avicel | 13 | — | 7 |
| Lactose | 78 | 47 | — |
| Starch (maize) | — | 9 | — |
| Starch (pregelatinised, NF15) | — | — | 32 |
| Sodium starch glycollate | 5 | — | — |
| Povidone | 3 | 3 | — |
| Magnesium stearate | 1 | 1 | 1 |
| | 125 | 85 | 65 |

| | Mg/tablet | |
|---|---|---|
| (ii) Sublingual | D | E |
| Active ingredient | 25 | 25 |
| Avicel | 10 | — |
| Lactose | — | 36 |
| Mannitol | 51 | 57 |
| Sucrose | — | 3 |
| Acacia - | | 3 |

-continued

| (1) Tablet formulations | | |
|---|---|---|
| Povidone | 3 | — |
| Magnesium stearate | 1 | 1 |
| | 90 | 125 |

Formulations A to E may be prepared by wet granulation of he first six ingredients with the povidone, followed by addition of the magnesium stearate and compression.

| (ii) Buccal | Mg/tablet |
|---|---|
| Active ingredient | 25 |
| Hydroxypropylmethyl cellulose (HPMC) | 25 |
| Polycarbophil | 39 |
| Magnesium stearate | 1 |
| | 90 |

The formulation may be prepared by direct compression of the admixed ingredients.

| (2) Capsule formulations | | |
|---|---|---|
| | Mg/Capsule | |
| (i) Powder | F | G |
| Active ingredient | 25 | 25 |
| Avicel | 45 | — |
| Lactose | 153 | — |
| Starch (1500 NF) | — | 117 |
| Sodium starch glycollate | — | 6 |
| Magnesium stearate | 2 | 2 |
| | 225 | 150 |

Formulations F and G may be prepared by adding the ingredients and filling two-part hard gelatin capsules with the resulting mixture.

| | Mg/Capsule | |
|---|---|---|
| (ii) Liquid fill | H | I |
| Active ingredient | 25 | 25 |
| Macrogol 4000 BP | 200 | — |
| Lecithin | — | 100 |
| Arachis oil | — | 100 |
| | 225 | 225 |

Formulation H may be prepared by melting the Macrogol 4000 BP, dispersing the active ingredient in the melt and filling two-pall hard gelatin capsules therewith. Formulation I may be prepared by dispersing the active ingredient in the lecithin and arachis oil and filling soft, elastic gelatin capsules with the dispersion.

| (iii) Controlled release | Mg/tablet |
|---|---|
| Active ingredient | 25 |
| Avicel | 123 |
| Lactose | 62 |
| Triethylcitrate | 3 |
| Ethyl cellulose | 12 |
| | 225 |

The formulation may be prepared by mixing and extruding the first four ingredients and spheronising and drying the extrudate. The dried pellets are coated with ethyl cellulose as a release controlling membrane and filled into two-part hard gelatin capsules.

| (3) Intravenous injection formulation | |
|---|---|
| | % by weight |
| Active ingredient | 2% |
| Hydrochloric acid ) | q.s to pH 7 |
| Citrate buffer) | |
| Water for Injections | to 100% |

The active ingredient is taken up in the citrate buffer and sufficient hydrochloric acid added to affect solution and adjust the pH to 7. The resulting solution is made up to volume and filtered through a micropore filter into sterile glass vials which are scaled and overscaled.

BIOLOGICAL EXAMPLES a) Investigation of Prodrug Activity in Rats of Compound of Example 6

Investigations were carried out in rats to determine whether 4-[1-Acetyl-3-[2-(dimethylamino)ethyl]indol-5-ylmethyl]oxazolidin-2-one acetate (compound of Example 6) acts as a prodrug for the pharmacologically active compound 4-[3-[2-(dimethylamino)ethyl]-1H-indol-5-ylmethyl]-2-oxazolidinone described in EP-A-0486666. The compound of Example 6 was incubated with rat plasma at a concentration of approx. 0.2 μg/ml for up to 4 h. At selected times the incubations were terminated by addition of acetone and the concentrations of both 4-[1-Acetyl-3-[2-(dimethylamino)ethyl]indol-5-ylmethyl]oxazolidin-2-one acetate and its breakdown product 4-[3-[2-(dimethylamino) ethyl]-1H-indol-5-ylmethyl]-2-oxazolidinone were determined by HPLC assay. In addition rats were administered 4-[1-Acetyl-3-[2-(dimethylamino)ethyl]indol-5-ylmethyl] oxazolidin-2-one acetate intravenously at a dose of 4 mg/kg and the plasma and brain concentrations of this compound and the breakdown product, 4-[3-[2-(Dimethylamino)ethyl]-1H-indol-5-ylmethyl]- 2-oxazolidinone were determined up to 8 h after administration.

4-[1-Acetyl-3-[2-(dimethylamino)ethyl]indol-5-ylmethyl]oxazolidin-2-one acetate was converted to 4-[3-[2-(Dimethylamino)ethyl]-1H-indol-5-ylmethyl]-2-oxazolidinone in rat plasma, with a half-life of approximately 3 h. After 4 h incubation only 30% of the parent compound of example 6 remained.

After intravenous administration, the peak plasma concentration (Cmax) of 4-[1-acetyl-3-[2-(dimethylamino) ethyl]indol-5-ylmethyl]oxazolidin-2-one acetate was approx 0.2 μg/ml (5 min) and this parent compound was detectable up to 1 h post dose (limit of detection 0.02 μg/ml); the plasma half-life was approximately 0.2 h. The breakdown product, 4-[3-[2-(dimethylamino) ethyl]-1H-indol-5-ylmethyl]-2-oxazolidinone was also detected in the plasma (Cmax 0.3 μg/ml, 5 min) up to 4 h after dosage.

These experiments demonstrate that 4-[1-acetyl-3-[2-(dimethylamino)ethyl]indol-5-yl-methyl]oxazolidin-2-one acetate is converted into 4-[3-[2-(dimethylamino)ethyl]-1H-indol-5-ylmethyl]-2-oxazolidinone in rats.

b) Investigation of Product Activity of Compound of Example 3

The compound of Example 3 was incubated with rat hepalocytes to determine whether the active compound, 4-[3-[2-(dimethylamino)ethyl]-1H-indol-5-ylmethyl]-2-oxazolidinone, is a main product of its metabolism. After 30 minutes incubation, no compound of Example 3 remained, while approximately 50% had been converted to the active compound.

These results indicate that the compound of Example 3 is extensively and rapidly converted into the active compound.

c) Investigation of Trans-Cellular Absorption of Compound of Example 3

The diffusion rates of the Compound of Example 3 and the active compound, 4-[3-[2-dimethylamino)ethyl]-1H-indol-5-ylmethyl]-2-oxazolidinone, through a lipoidal membrane barrier (laceryl alcohol/caprytic acid lipid membrane) were determined and compared. The results were:

|  | Diffusion Rate (cm/min/1000) |
| --- | --- |
| Compound of Example 3 | 3.88 |
| Active compound | 0.68 |

These results indicate that the Compound of Example 3 may be significantly more efficiently absorbed via transcellular mechanisms than the active compound of which it is a prodrug.

What is claimed is:

1. A method for the prophylaxis or treatment of a clinical condition in a mammal, such as a human, for which a 5-HT$_1$-like receptor is indicated, said method comprising the administration to said mammal of a therapeutically effective amount of a compound of the following formula,

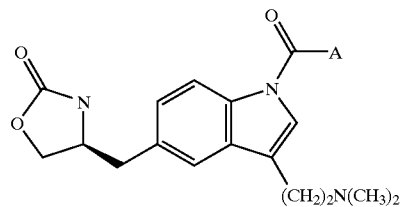

wherein

A is $C_{1-6}$alkyl, —O—$C_{1-6}$alkyl, or —O—phenyl, or phenyl where any said phenyl may have a substituent selected from $C_{1-3}$alkyl or halogen.

2. The method of claim 1, wherien said clinical condition for which a 5-HT$_1$-like receptor agonist is indicated is selected from mugrane, cluster headache and headache associated with vascular disorders.

3. The method of claim 1, for treatment of said clinical condition.

4. The method of claim 1, wherein said compound is incorporated into a pharmaceutical composition comprising said compound and at least one pharmaceutically-acceptable carrier or excipient.

5. The method according to claim 1, wherein said therapeutically-effective amount is an amount of said compound sufficient to release after administration a therapeutically-effective amount of a compound of the following formula:

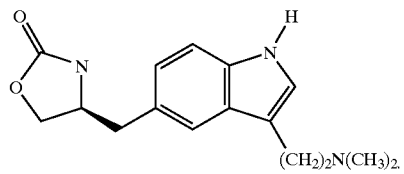

* * * * *